United States Patent
Shabaan et al.

(10) Patent No.: US 11,814,346 B1
(45) Date of Patent: Nov. 14, 2023

(54) CHARGE TRANSPORTATION IN NANOSTRUCTURED FUNCTIONAL SELENIUM-CONTAINING LIQUID CRYSTALLINE MATERIALS

(71) Applicant: KING FAISAL UNIVERSITY, Al-Ahsa (SA)

(72) Inventors: Saadeldin Elsayed Ibrahim Shabaan, Al-Ahsa (SA); Hany Mohamed Abd El-Lateef Ahmed, Al-Ahsa (SA); Mohamed Alaasar, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/212,483

(22) Filed: Jun. 21, 2023

(51) Int. Cl.
- *C07C 391/02* (2006.01)
- *C07C 67/465* (2006.01)
- *C07C 45/61* (2006.01)
- *C09K 19/06* (2006.01)
- *H10K 85/00* (2023.01)
- *H10K 85/60* (2023.01)
- *H10K 30/85* (2023.01)
- *C09K 19/04* (2006.01)

(52) U.S. Cl.
CPC ............ *C07C 391/02* (2013.01); *C07C 45/61* (2013.01); *C07C 67/465* (2013.01); *C09K 19/06* (2013.01); *H10K 85/60* (2023.02); *H10K 85/731* (2023.02); *C09K 2019/0437* (2013.01); *H10K 30/85* (2023.02)

(58) Field of Classification Search
None
See application file for complete search history.

(56) References Cited

U.S. PATENT DOCUMENTS

| | | | |
|---|---|---|---|
| 10,106,497 B2 * | 10/2018 | Dyballa | ............... C07C 391/02 |
| 2003/0003300 A1 | 1/2003 | Korgel et al. | |
| 2006/0241220 A1 | 10/2006 | Li et al. | |
| 2009/0074649 A1 | 3/2009 | Korgel et al. | |
| 2010/0127215 A1 | 5/2010 | Boerner et al. | |

OTHER PUBLICATIONS

Jamain, et al., "Synthesis and Determination of Thermotropic Liquid Crystalline Behavior of Cinnamaldehyde-Based Molecules with Two Schiff Base Linking Units", Molecules 2020, 25(17), 3780.

Kaushal, et al., "Click chemistry in the synthesis of catalytically relevant organoselenium compounds: development and applications of catalysts for organic synthesis", New J. Chem., 2022,46, 14757-14781.

\* cited by examiner

*Primary Examiner* — Joseph R Kosack
(74) *Attorney, Agent, or Firm* — Nath, Goldberg & Meyer; Richard C. Litman

(57) ABSTRACT

Novel Schiff base and diazo liquid crystals with a selenium center forming nanostructured $Cub_{bi}$ phases are presented herein. The new liquid crystals can be used for the fabrication of high-performance photovoltaic devices, while exhibiting improved thermal stability and electron-transport properties as compared to currently known liquid crystals.

20 Claims, No Drawings

CHARGE TRANSPORTATION IN NANOSTRUCTURED FUNCTIONAL SELENIUM-CONTAINING LIQUID CRYSTALLINE MATERIALS

BACKGROUND

1. Field

The disclosure of the present patent application relates to novel Schiff base and diazo liquid crystals with a selenium center forming nanostructured $Cub_{bi}$ phases.

2. Description of the Related Art

Soft self-assembly of small molecules into stimuli-responsive nanostructured soft matter structures is an important route to obtaining new functional materials. Liquid crystals (LCs) represent one class of such materials, which have not only been applied in Liquid Crystal Displays (LCDs) but also for steerable antennas in satellite and 5G communication systems, as well as serving as responsive materials for biosensors and photonic applications.

Moreover, LCs have been used recently as charge carrier materials with adjustable and switchable conduction pathways for ions, electrons, and holes. Bicontinuous cubic ($Cub_{bi}$) LC phases are nanosegregated networks, which form continuous conduction channels in three dimensions, thus minimizing distortions occurring in the case of ion carrying ionic amphiphiles. For electron/hole carriers, the conduction pathways in all three spatial dimensions are expected to provide an additional entropic advantage for charge separation. The design of electron/hole carrier systems requires extended π-conjugated cores, which usually results in LC phases other than the desired nanostructured $Cub_{bi}$ phases.

Thus, new molecules capable of forming the desired $Cub_{bi}$ phase liquid crystal materials solving the aforementioned problems are desired.

SUMMARY

The present subject matter relates to the design of charge transfer Schiff base and diazo tethered organoselenium (Se)-based liquid crystals (SeLCs) which are unique, have not been reported before, and offer the potential for the fabrication of high-performance photovoltaic devices. Furthermore, the present multichain SeLCs are expected to exhibit improved thermal stability and electron-transport properties compared to currently known liquid crystals (LCs).

In an embodiment, the present subject matter relates to a Schiff base organoselenium-based liquid crystal having the formula I:

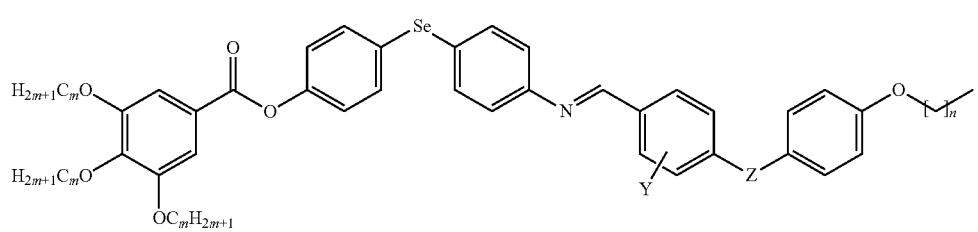

wherein:

Z is O, N, S, or Se;

Y is H, COOH, COOMe, COOEt, $NO_2$, CN, F, Cl, Me, Et, OMe, or OEt;

m is an integer between 6 and 10; and n is an integer from 2 to 18.

In a further embodiment, the present subject matter relates to a method of making the Schiff base organoselenium-based liquid crystal as described herein, the method comprising: 1) reacting a 4-halobenzaldehyde with an alkyloxy phenyl in DMSO to obtain an aldehyde according to the following reaction scheme:

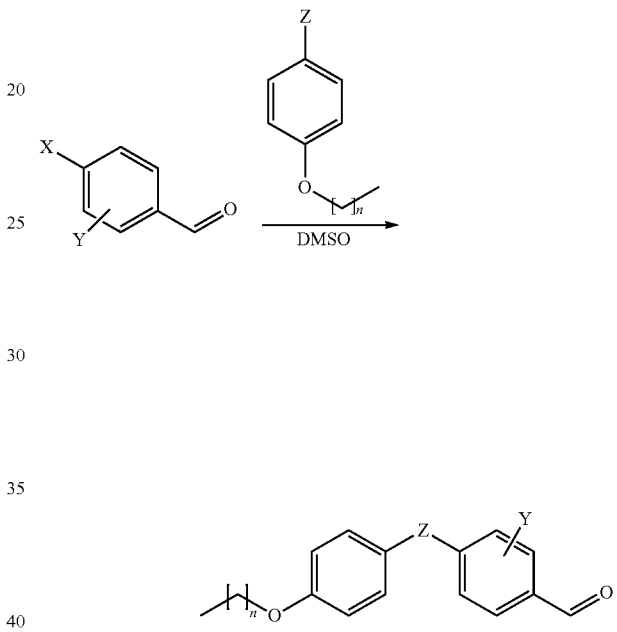

wherein:

X is F or I;

Z is O, N, S, or Se;

Y is H, COOH, COOMe, COOEt, $NO_2$, CN, F, Cl, Me, Et, OMe, or OEt;

m is an integer between 6 and 10; and n is an integer from 2 to 18;

2) reacting the aldehyde with 4,4'-diselanediyldianiline in ethanol with catalytic amounts of acetic acid to obtain a bis-Schiff base according to the following reaction scheme:

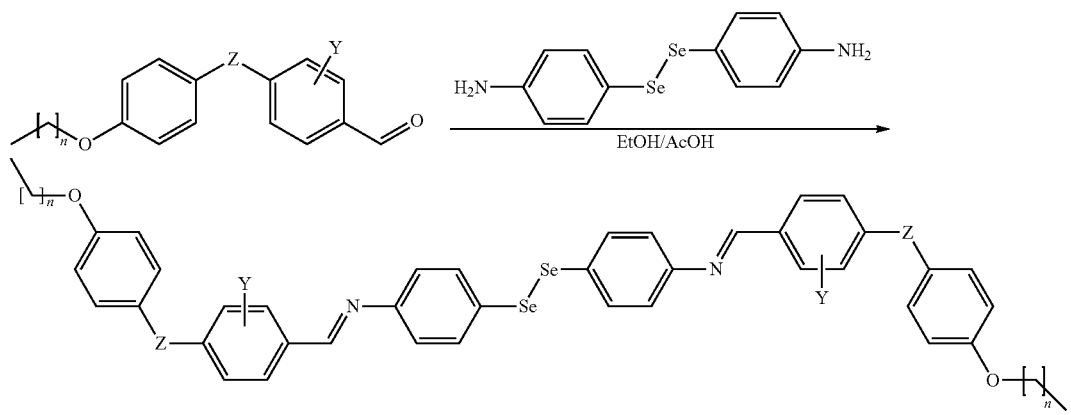

3) reacting the bis-Schiff base with a halophenyl with copper iron oxide and KOH as catalysts in DMSO to obtain a selenide according to the following reaction scheme:

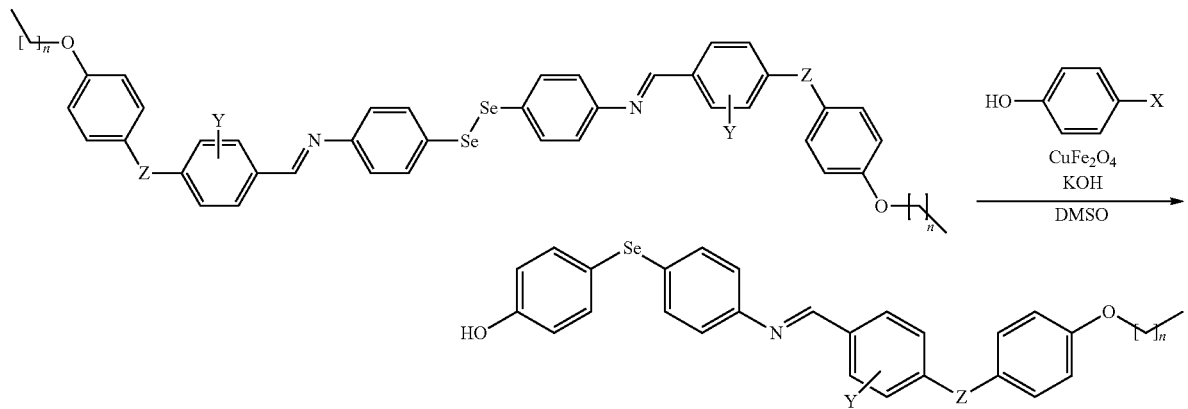

and 4) heating a tri-substituted benzoic acid with SOCl$_2$ in dichloromethane, followed by reaction with the selenide using triethylamine and a catalytic amount of dry pyridine to obtain the Schiff base organoselenium-based liquid crystal according to the following reaction scheme:

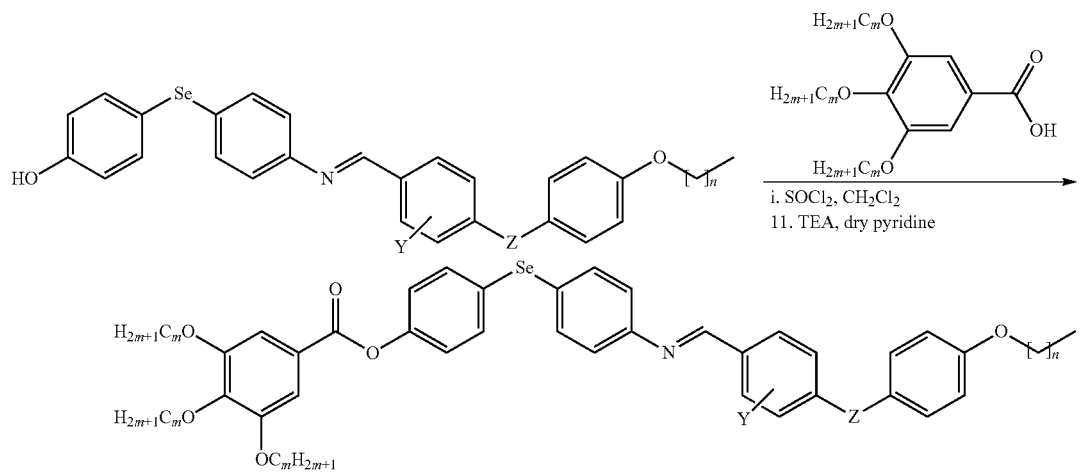

In another embodiment, the present subject matter relates to a diazo organoselenium-based liquid crystal having the formula II:

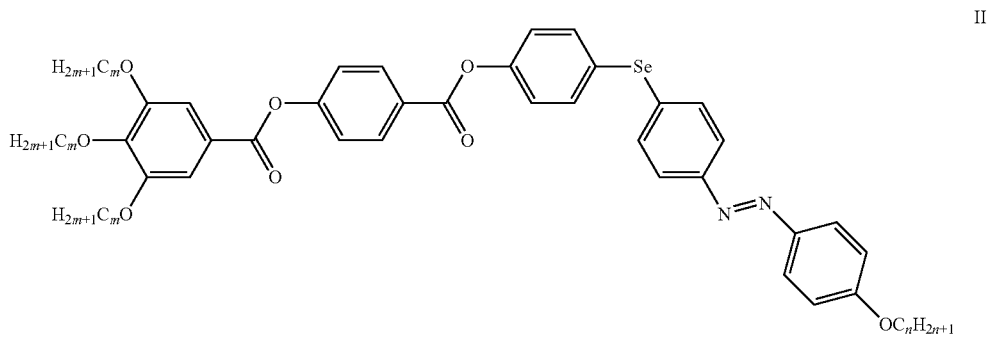

II wherein:
m is an integer between 6 and 10; and
n is an integer from 4 to 20.

In still another embodiment, the present subject matter relates to a method of making the diazo organoselenium-based liquid crystal as described herein, the method comprising: 1) bis diazo-coupling a diselenide diamine and a phenol using $NaNO_2$ and HCl to obtain a first diselenide according to the following reaction scheme:

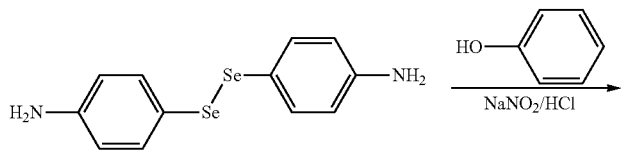

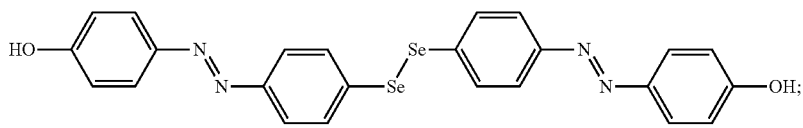

2) reacting the first diselenide with an alkyl bromide in 2-butanone using $K_2CO_3$ as a catalyst with heating at a temperature of about 80° C., followed by reaction in ethanol with KOH with heating at a temperature of about 85° C. to obtain a second diselenide according to the following reaction scheme:

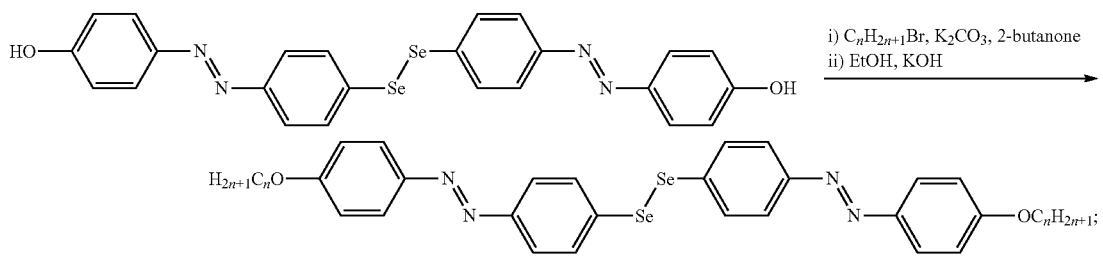

wherein:
  m is an integer between 6 and 10; and
  n is an integer from 4 to 20;
3) reacting the second diselenide with 4-iodophenyl and copper iron oxide and KOH as catalysts in DMSO to obtain a selenide according to the following reaction scheme:

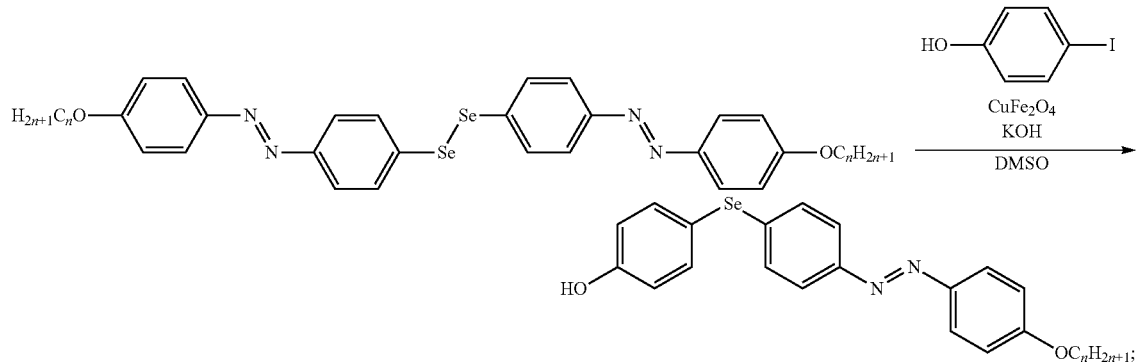

4) reacting a first trisubstituted benzoic acid with 4-formyl benzoic acid using dicyclohexyl carbodiimide (DCC) followed by oxidation using $CrO_3$ as a catalyst to obtain a second trisubstituted benzoic acid according to the following reaction scheme:

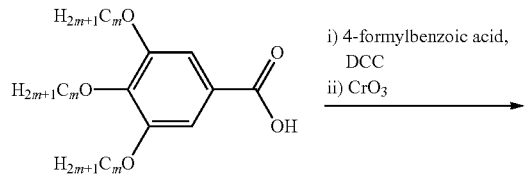

-continued

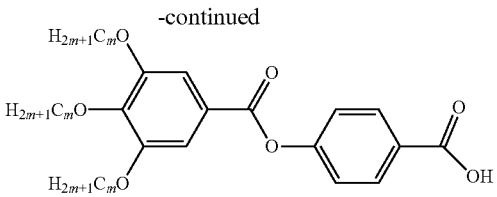

and 5) heating the second trisubstituted benzoic acid with $SOCl_2$ in dichloromethane followed by reacting with the selenide using triethylamine and a catalytic amount of dry pyridine to obtain the diazo organoselenium-based liquid crystal according to the following reaction scheme:

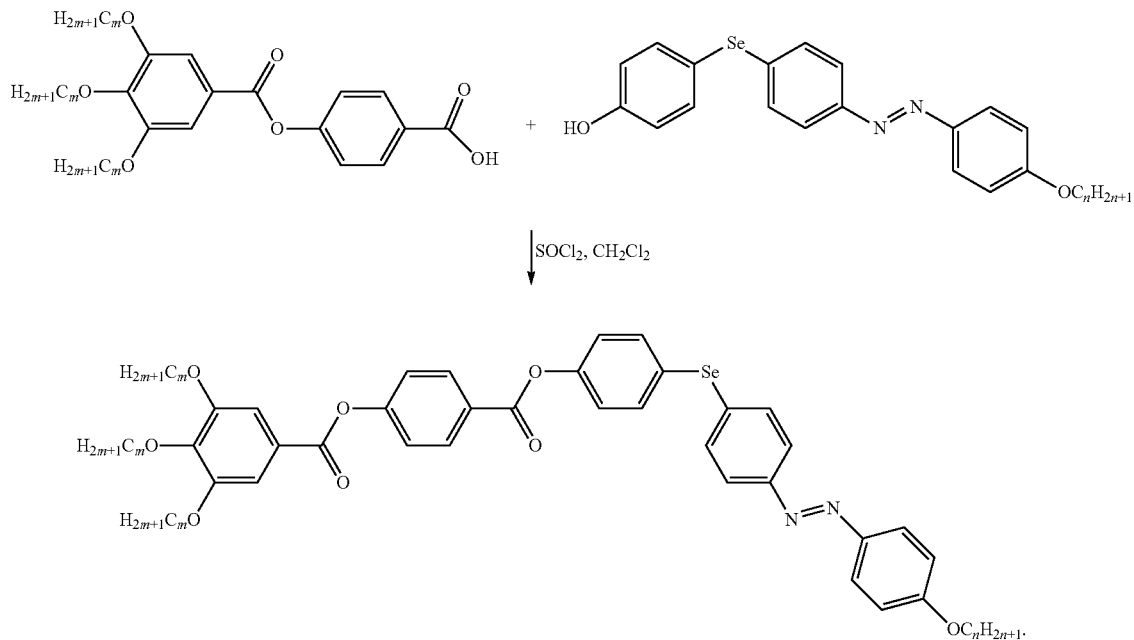

In a further embodiment, the present subject matter relates to a semiconducting liquid crystalline material comprising the Schiff base organoselenium-based liquid crystal or the diazo organoselenium-based liquid crystal as described herein.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

The present subject matter relates to novel Schiff base and diazo liquid crystals with a selenium (Se) center forming nanostructured Cub$_{bi}$ phases. The target materials have four terminal alkyl chains distributed non symmetrically at both ends of an elongated aromatic backbone. Moreover, the phase behaviour will be modified by introducing an additional lateral substituent (Y).

The present selenium liquid crystals (SeLCs) can be utilized to provide improved charge extraction and charge mobility compared to nitrogen, oxygen, and sulfur-containing LCs because of the Se atom unique properties. The large size of the Se atom (118 pm) compared to that of oxygen (64 pm), nitrogen (65 pm), and sulfur (104 pm) would be expected to improve the corresponding intermolecular interactions owing to the enhanced Se interactions emerged from its bigger atomic size. Moreover, SeLCs are expected to manifest narrower bandgaps due to the high polarizability nature of Se, which in turn will improve electron delocalization and therefore better conjugation. Furthermore, the Schiff base (CH=N—) and the diazo (N=N) moieties retain the rigidity of the geometrical shape thus enhancing the mesophase thermal stability.

Accordingly, in an embodiment, the present subject matter relates to a Schiff base organoselenium-based liquid crystal having the formula I:

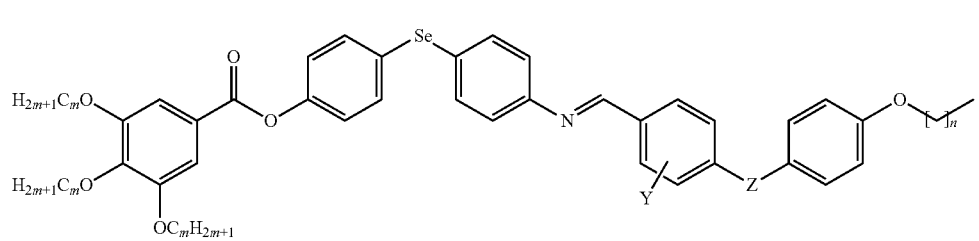

I wherein:
Z is O, N, S, or Se;
Y is H, COOH, COOMe, COOEt, NO$_2$, CN, F, Cl, Me, Et, OMe, or OEt;
m is an integer between 6 and 10; and
n is an integer from 2 to 18.

In this regard, the variables for the Schiff base organoselenium-based liquid crystal of formula I can be defined as follows:
Z is O;
Y is H;
m is 10; and
n is 4.

Stated differently, the Schiff base organoselenium-based liquid crystal can have the formula:

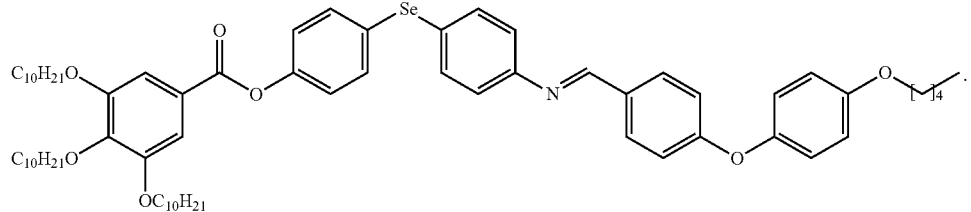

In a further embodiment, the present subject matter relates to a method of making the Schiff base organoselenium-based liquid crystal as described herein, the method comprising: 1) reacting a 4-halobenzaldehyde with an alkyloxy phenyl in DMSO to obtain an aldehyde according to the following reaction scheme:

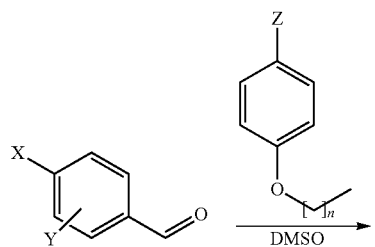

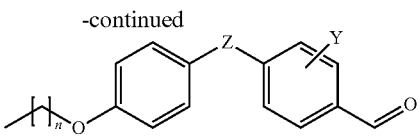

wherein:
X is F or I;
Z is O, N, S, or Se;
Y is H, COOH, COOMe, COOEt, NO$_2$, CN, F, Cl, Me, Et, OMe, or OEt;
m is an integer between 6 and 10; and
n is an integer from 2 to 18;

2) reacting the aldehyde with 4,4'-diselanediyldianiline in ethanol with catalytic amounts of acetic acid to obtain a bis-Schiff base according to the following reaction scheme:

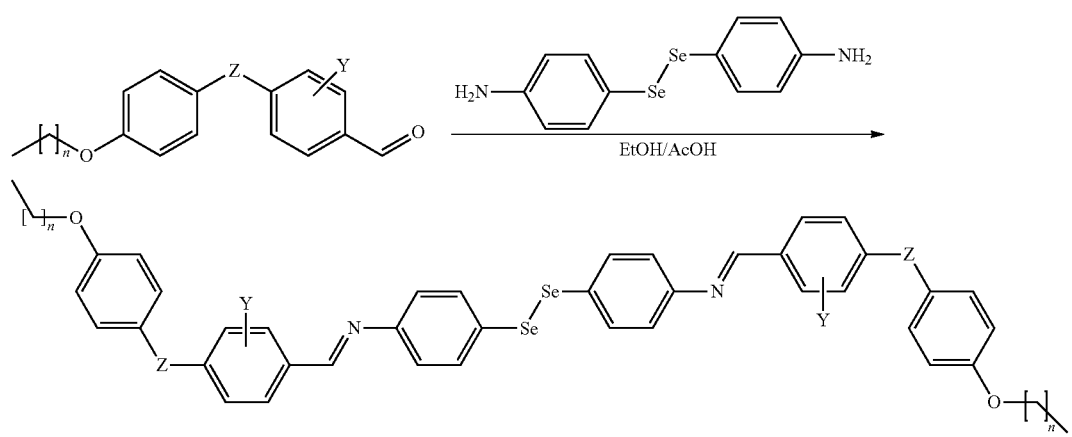

3) reacting the bis-Schiff base with a halophenyl with copper iron oxide and KOH as catalysts in DMSO to obtain a selenide according to the following reaction scheme:

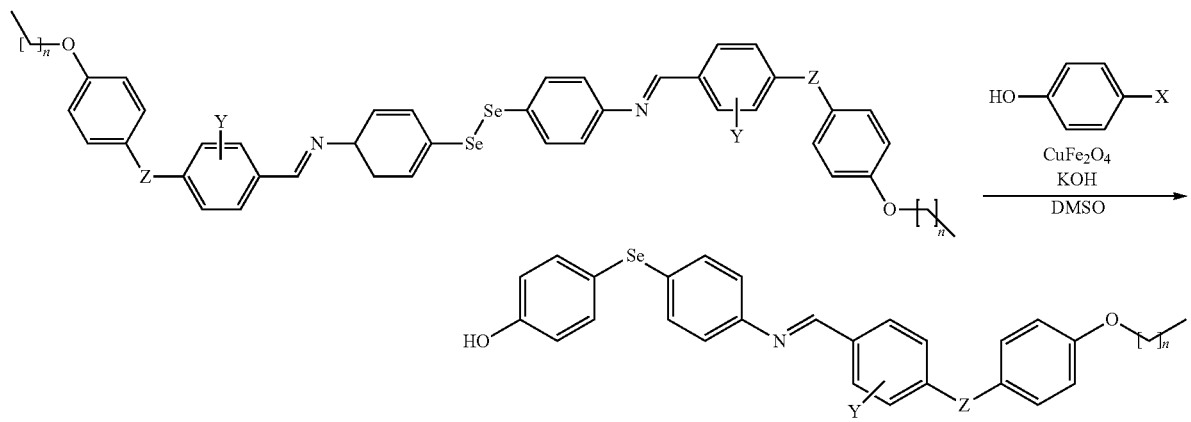

and
4) heating a tri-substituted benzoic acid with SOCl$_2$ in dichloromethane, followed by reaction with the selenide using triethylamine (TEA) and a catalytic amount of dry pyridine to obtain the Schiff base organoselenium-based liquid crystal according to the following reaction scheme:

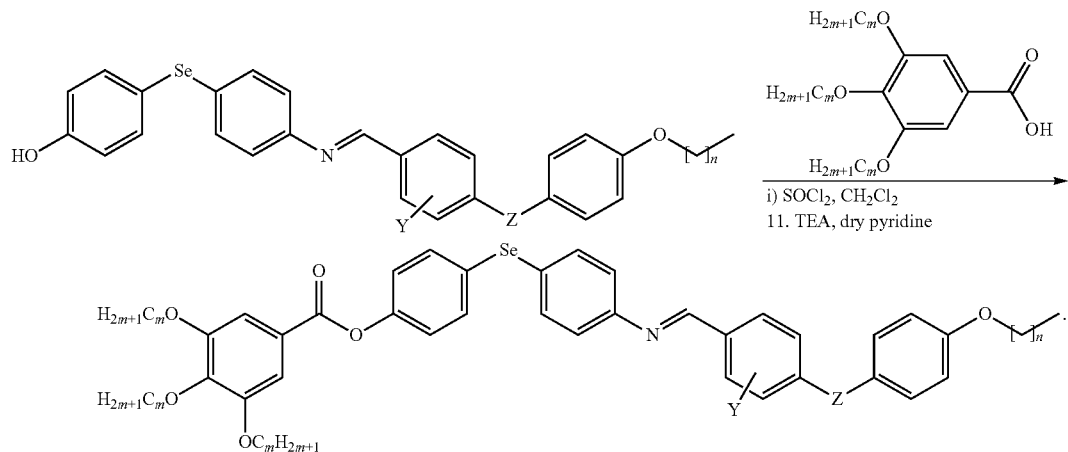

It is further contemplated herein that each step of this method can be used on its own if the starting materials of the step are otherwise available. By way of non-limiting example, the Schiff base organoselenium-based liquid crystal can be made by the method of step 4 only, provided all of the tri-substituted benzoic acid, SOCl$_2$, dichloromethane, selenide, triethylamine, and dry pyridine are otherwise available.

In an embodiment, in step 1 of this method, the 4-halobenzaldehyde and the alkyloxy phenyl can be reacted in an about 1:1 molar ratio under nitrogen and at a temperature of about 70° C. to about 90° C., about 70° C., about 75° C., about 80° C., about 85° C., about 90° C., or about 80° C. In this regard, about 1 mmol of each of the 4-halobenzaldehyde and the alkyloxy phenyl can be used in step 1 of this method. In addition, this step of the present method can be conducted for at least about 4 hours to provide the aldehyde.

In another embodiment, in step 2 of this method, 0.5 equivalents of the 4,4'-diselanediyldianiline are used.

In a further embodiment, in step 3 of this method, the bis-Schiff base and the halophenyl are reacted in an about 1:2 molar ratio at a temperature of about 110° C. to about 130° C., about 110° C., about 115° C., about 120° C., about 125° C., about 130° C., or about 120° C. In this regard, about 0.5 mmol of the bis-Schiff base and about 1 mmol of the halophenyl can be used in step 3 of this method. In another embodiment, the catalysts copper iron oxide and KOH can be used at about 5 mol % and about 1 mmol, respectively, i.e., the KOH can be used in an about 1:1 molar ratio with the halophenyl. In addition, this step of the present method can be conducted for at least about 18 hours to obtain the selenide.

In still another embodiment, in step 4 of this method, the tri-substituted benzoic acid and the SOCl$_2$ in the dichloromethane are heated at a temperature of about 35° C. to about 45° C., about 35° C., about 40° C., about 45° C., or about 40° C. with the tri-substituted benzoic acid, the $SOCl_2$, and the selenide being reacted in an about 1:3:0.9 molar ratio. In this regard, about 1 mmol of the tri-substituted benzoic acid, about 3 mmol of the $SOCl_2$, and about 0.9 mmol of the selenide can be used in step 4 of this method. In another embodiment, the TEA can be used at about 1 mmol, i.e., the TEA can be used in an about 1:1 molar ratio with the tri-substituted benzoic acid.

In another embodiment, the present subject matter relates to a diazo organoselenium-based liquid crystal having the formula II:

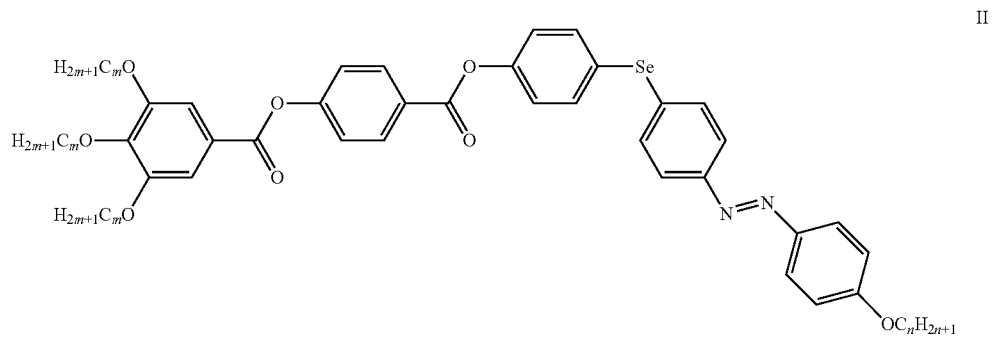

II wherein:
  m is an integer between 6 and 10; and
  n is an integer from 4 to 20.

In this regard, the variables for the diazo organoselenium-based liquid crystal of formula I can be defined as follows:
  m is 10; and
  n is 5.

Stated differently, the diazo organoselenium-based liquid crystal can have the formula:

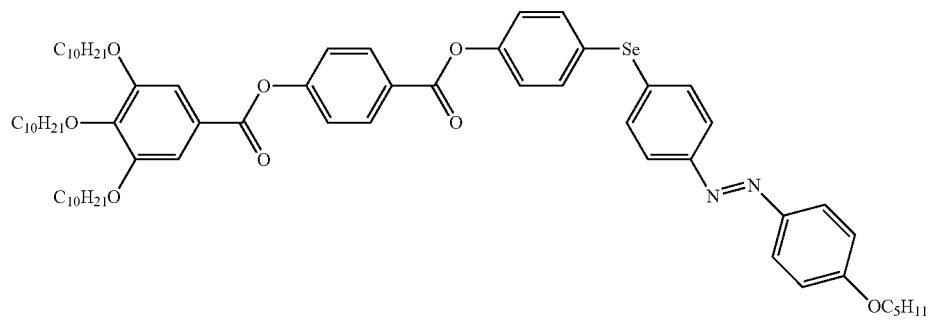

In still another embodiment, the present subject matter relates to a method of making the diazo organoselenium-based liquid crystal as described herein, the method comprising: 1) bis diazo-coupling a diselenide diamine and a phenol using NaNO$_2$ and HCl to obtain a first diselenide according to the following reaction scheme:

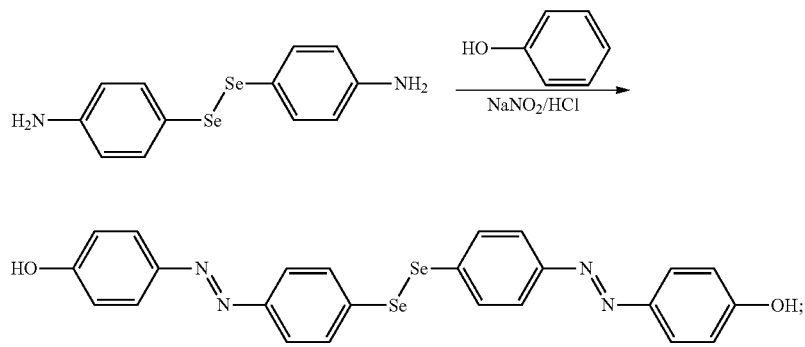

2) reacting the first diselenide with an alkyl bromide in 2-butanone using K$_2$CO$_3$ as a catalyst with heating at a temperature of about 80° C., followed by reaction in ethanol with KOH with heating at a temperature of about 85° C. to obtain a second diselenide according to the following reaction scheme:

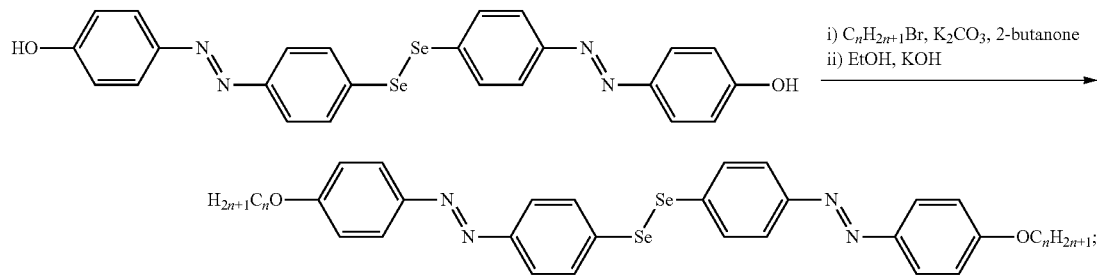

wherein:
 m is an integer between 6 and 10; and
 n is an integer from 4 to 20;
3) reacting the second diselenide with 4-iodophenyl and copper iron oxide and KOH as catalysts in DMSO to obtain a selenide according to the following reaction scheme:

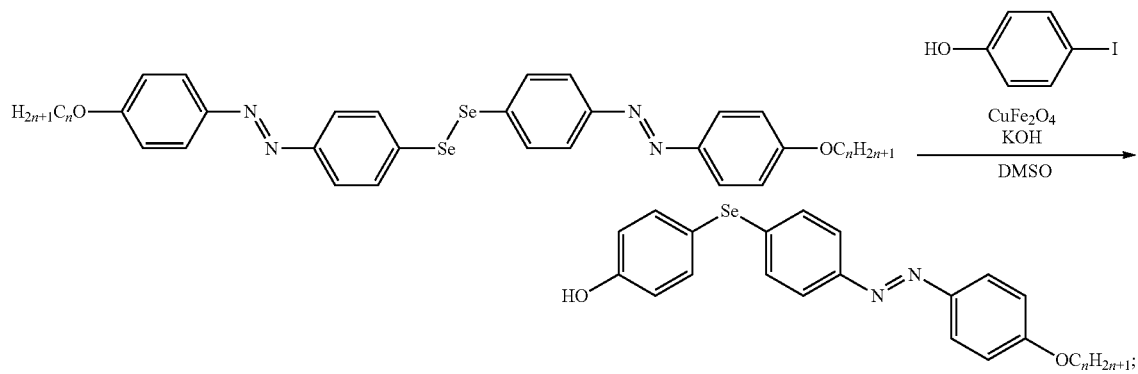

4) reacting a first trisubstituted benzoic acid with 4-formyl benzoic acid using dicyclohexyl carbodiimide (DCC) followed by oxidation using $CrO_3$ as a catalyst to obtain a second trisubstituted benzoic acid according to the following reaction scheme:

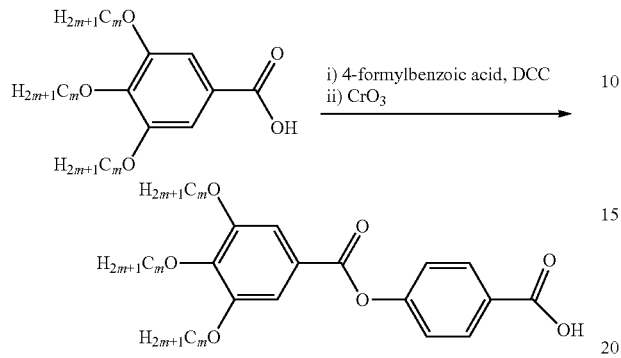

and 5) heating the second trisubstituted benzoic acid with $SOCl_2$ in dichloromethane followed by reacting with the selenide using triethylamine and a catalytic amount of dry pyridine to obtain the diazo organoselenium-based liquid crystal according to the following reaction scheme:

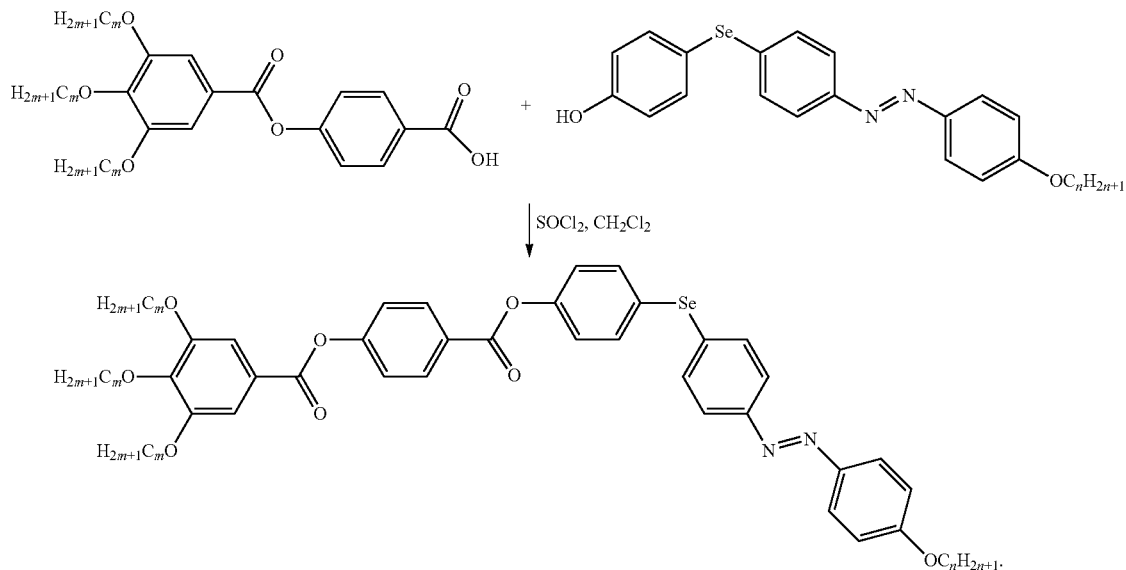

It is further contemplated herein that each step of this method can be used on its own if the starting materials of the step are otherwise available. By way of non-limiting example, the diazo organoselenium-based liquid crystal can be made by the method of step 5 only, provided all of the tri-substituted benzoic acid, $SOCl_2$, dichloromethane, selenide, triethylamine, and dry pyridine are otherwise available.

In an embodiment, in step 1 of this method, the diselenide diamine and the phenol can be reacted in an about 1:2.2 molar ratio under nitrogen and at a temperature of about 0° C. to about 5° C. In this regard, about 1 mmol of the diselenide diamine and about 2.2 mmol of the phenol can be used in step 1 of this method. In another embodiment, the $NaNO_2$ can be used at about 2.5 mmol, i.e., the $NaNO_2$ can be used in an about 2.5:1 molar ratio with the diselenide diamine.

In another embodiment, in step 2 of this method, the first diselenide and the alkyl bromide can be reacted in an about 1:2.2 molar ratio. In this regard, about 1 mmol of the first diselenide and about 2.2 mmol of the alkyl bromide can be used in step 2 of this method. This step can be bifurcated into two steps: first, the 2-butanone can be used as a solvent with the $K_2CO_3$ being used as a catalyst with heating at a temperature of about 80° C., followed by conducting a reaction in ethanol with KOH with heating at a temperature of about 85° C. to obtain the second diselenide.

In another embodiment, in the first part of this step, the $K_2CO_3$ can be used at about 2 mmol, i.e., the $K_2CO_3$ can be used in an about 2:1 molar ratio with the first diselenide. Further, the first part of this step can be conducted for at least about 18 hours.

In the second part of this step, the KOH can be used at about 2 mmol, i.e., the KOH can be used in an about 2:1 molar ratio with the first diselenide. Further, the second part of this step can be conducted for at least about 8 hours.

In a further embodiment, step 3 of this method can be conducted at a temperature of about 110° C. to about 130° C., about 110° C., about 115° C., about 120° C., about 125° C., about 130° C., or about 120° C. This step can be conducted for at least about 18 hours.

In still another embodiment, in step 4 of this method, the first trisubstituted benzoic acid and the DCC can be used in an about 1:1 molar ratio. In this regard, about 1 mmol of the first trisubstituted benzoic acid and about 1 mmol of the Dcc can be used in step 4 of this method. Further, the $CrO_3$ can be used at about 20 mol %.

In yet another embodiment, in step 5 of this method, the second trisubstituted benzoic acid and the $SOCl_2$ in the dichloromethane can be heated at a temperature of about 35° C. to about 45° C., about 35° C., about 40° C., about 45° C., or about 40° C. with the second trisubstituted benzoic acid, the $SOCl_2$, and the selenide being reacted in an about 1:3:0.9 molar ratio. In this regard, about 1 mmol of the second trisubstituted benzoic acid, about 3 mmol of the $SOCl_2$, and about 0.9 mmol of the selenide can be used in step 5 of this method. In another embodiment, the TEA can be used at about 1 mmol, i.e., the TEA can be used in an about 1:1 molar ratio with the second trisubstituted benzoic acid.

In a further embodiment, the present subject matter relates to a semiconducting liquid crystalline material comprising the Schiff base organoselenium-based liquid crystal or the diazo organoselenium-based liquid crystal as described herein. In this regard, the semiconducting liquid crystalline material can be a stimuli-responsive material for photophysical applications.

In this regard, the designed functional liquid crystalline materials described herein can form a wide variety of helical network phases, ranging from soft crystalline via bicontinuous cubic and noncubic 3D phases to mirror symmetry broken liquids. The cubic phases could cover wide temperature ranges including ambient temperature and the phase type can be controlled by adjusting the intermolecular twist along the networks by chain length modification. Further, these materials should be able to charge transport in all three spatial directions, which would be advantageous over the 1D transport in the currently known columnar phases or the 2D lamellar phases.

Organoselenium compounds have only been rarely used in liquid crystals (LCs). Accordingly, the present Schiff base and diazo LCs with a Se core forming nanostructured $Cub_{bi}$ phases are expected to display good thermal stability (decomposition temperatures >200° C.). The incorporation of the azomethine and the diazo units in the molecular structure is expected to achieve the required level of mobility and maintain rigidity, thus improving the mesophase thermal durability. Moreover, for the diazo liquid crystals, the diazo moiety is expected to give the possibility of fine tuning the molecular structure by light irradiation. As such, these liquid crystals may be used in different photonic applications requiring photoswitchable materials.

By light irradiation in the case of photo responsive materials, further tuning of the molecular structure can improve the charge transport properties in the bicontinuous networks. This can provide a new concept for semiconducting liquid crystalline materials by the 3D networks. In addition, the spontaneous mirror symmetry breaking in these cubic phases can provide uniformly helical soft matter structures and chiral liquids from achiral functional molecules. This can provide additional applications of the target materials going beyond their use as charge carrier materials, for example, as stimuli-responsive materials for photophysical applications like aggregation-induced polarized emission and light harvesting.

The present teachings are illustrated by the following examples.

EXAMPLES

Example 1

Preparation of Schiff Base Organoselenium-Based Liquid Crystal

A representative example for the synthesis of Schiff base organoselenium-based liquid crystals (SeLCs) is compound 8 shown in the reaction scheme below.

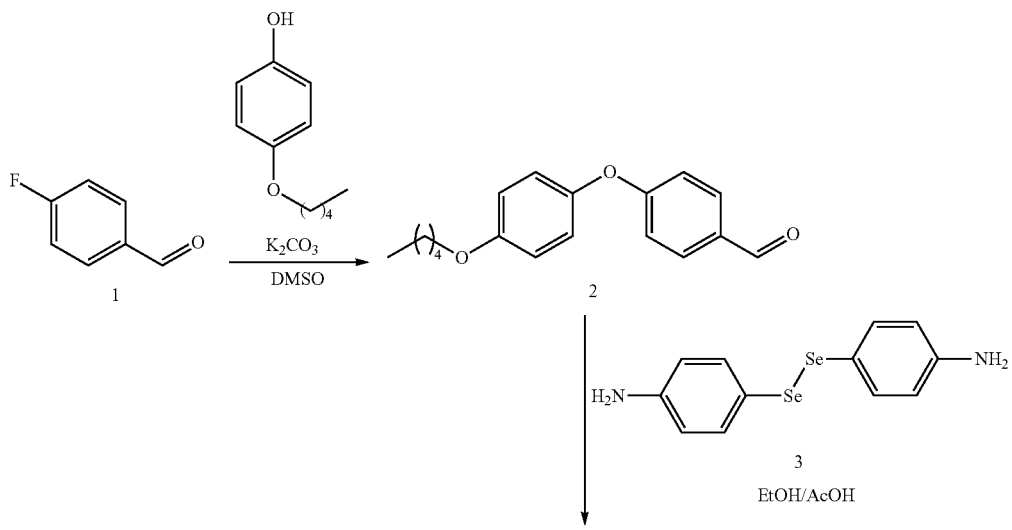

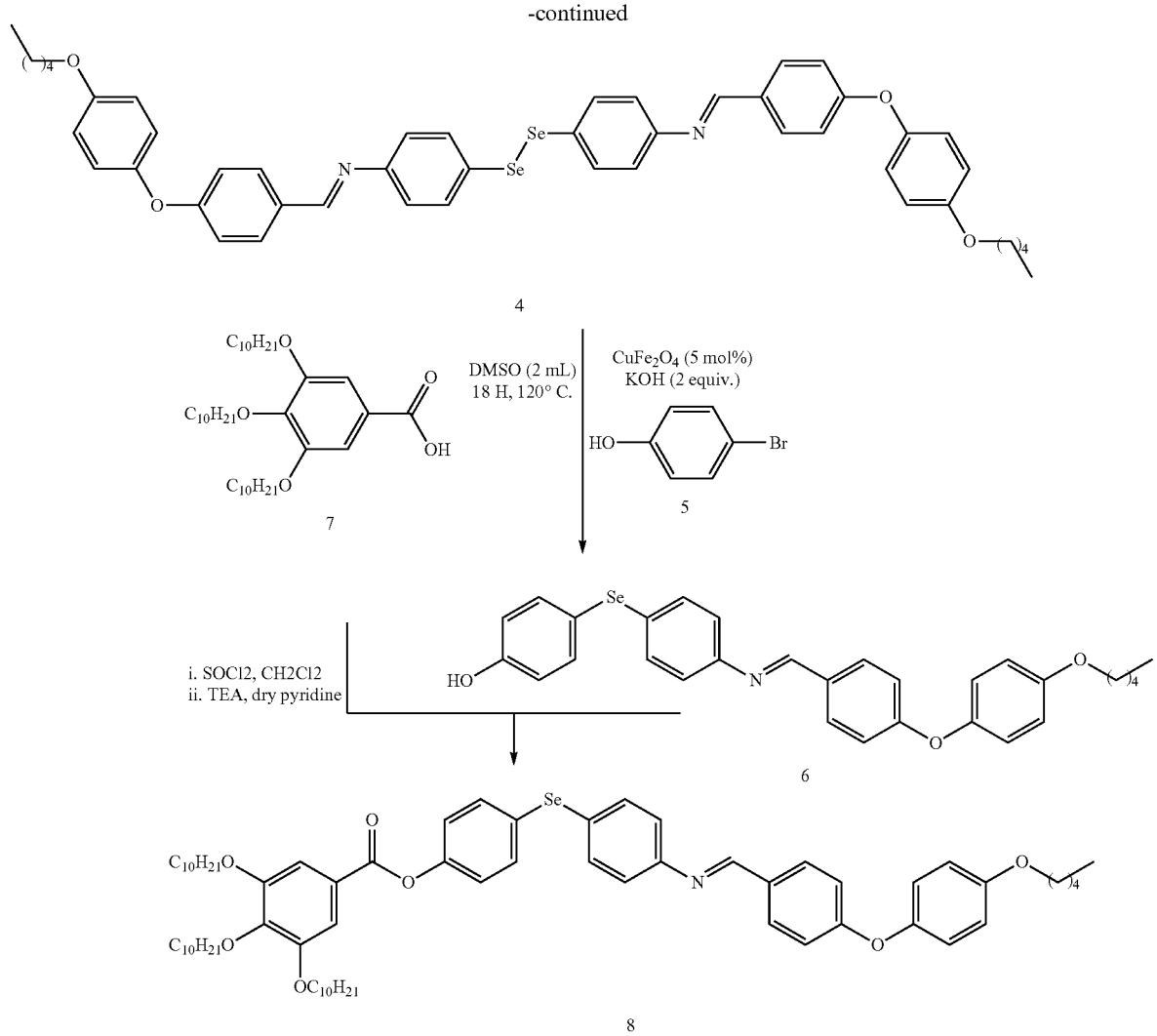

The Schiff base organoselenium-based liquid crystal is synthesized in four steps starting from the reaction of 4-fluorobenzaldehyde (1 mmol) and 4-butoxyphenol (1 mmol) in DMSO (2 ml), under nitrogen, and heating at 80° C. for 4 hours to give aldehyde 2. The aldehyde 2 is reacted with 0.5 equivalent of 4,4'-diselanediyldianiline (3) in ethanol (20 ml) and catalytic amounts of acetic acid to obtain the corresponding bis-Schiff base (4) as a diselenide. The reaction of diselenide 4 (0.5 mmol) and p-bromophenol (1 mmol) with copper iron oxide (5 mol %) and KOH (1 mmol) as the catalysts in DMSO (2 ml) at 120° C. for 18 hrs afforded the corresponding selenide 6. Heating of the tri-substituted benzoic acid 7 (1 mmol) with $SOCl_2$ (3 mmol) in dichloromethane at 40° C., followed by reaction with selenide 6 (0.9 mmol) using triethylamine (TEA, 1 mmol) and a catalytic amount of dry pyridine afforded compound 8.

Example 2

Synthesis of Diazo Organoselenium-Based Liquid Crystal

A representative example for the synthesis of diazo organoselenium-based liquid crystals (SeLCs) is compound 15 shown in the reaction scheme below.

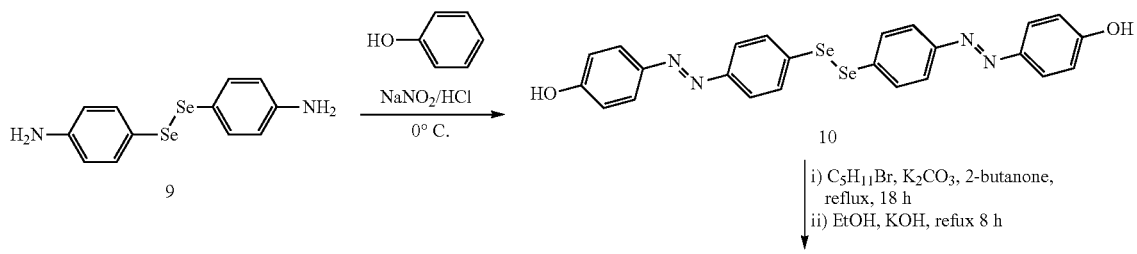

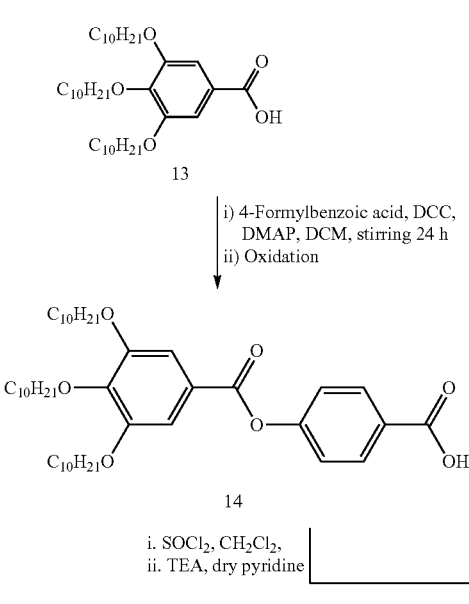

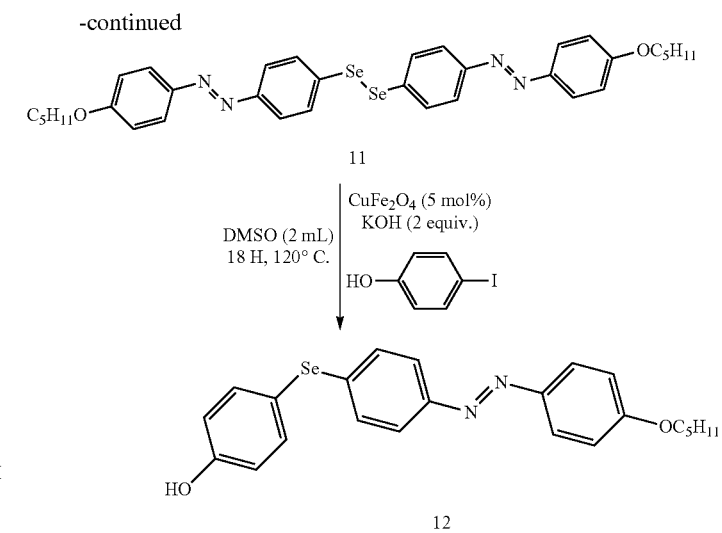

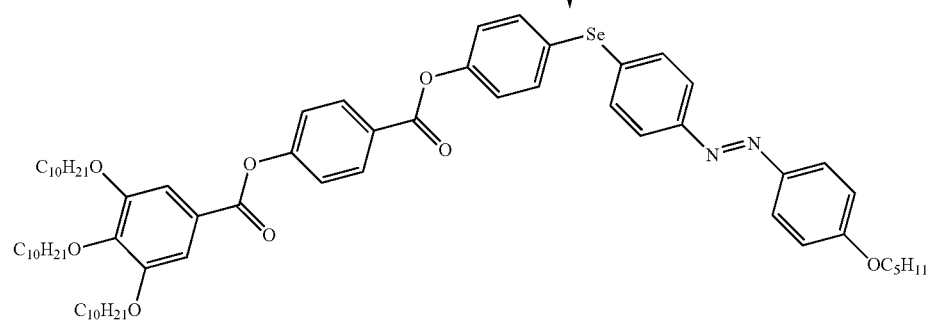

The synthesis of SeLC 15 proceeded in 5 steps. The first step started with the bis diazo-coupling reaction of the diamine 9 (1 mmol) and phenol (2.2 mmol) using NaNO$_2$ (2.5 mmol) and HCl (10 ml) following the typical azo-coupling protocol at 0-5° C. The resulting diselenide 10 (1 mmol) reaction with pentyl bromide (2.2 mmol) afforded compound 11, which proceeded in two steps; the first step included 2-butanone (10 ml) as the solvent and K$_2$CO$_3$ (2 mmol) as the catalyst and heating at 80° C. for 18 hrs. The second step proceeded in ethanol (10 ml) with the KOH (2 mmol) and heating at 85° C. for 8 hrs.

Furthermore, the reaction of diselenide 11 with 4-iodophenol (1 mmol) and copper iron oxide (5 mol %) and KOH (1 mmol) as the catalysts in DMSO (2 ml) at 120° C. for 18 hours afforded the corresponding selenide 12.

Separately, compound 14 was synthesized by the reaction of trisubstituted benzoic acid 13 (1 mmol) with 4-formyl benzoic acid using dicyclohexyl carbodiimide (DCC) (1 mmol) followed by oxidation using CrO$_3$ (20 mol %) as the catalyst.

Heating of the trisubstituted benzoic acid 14 (1 mmol) with SOCl$_2$ (3 mmol) in dichloromethane at 40° C., followed by a reaction with selenide 12 (0.9 mmol) using triethylamine (TEA, 1 mmol) and a catalytic amount of dry pyridine afforded compound 15.

It is to be understood that the Schiff base and diazo liquid crystals with a selenium center are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A Schiff base organoselenium-based liquid crystal having the formula I:

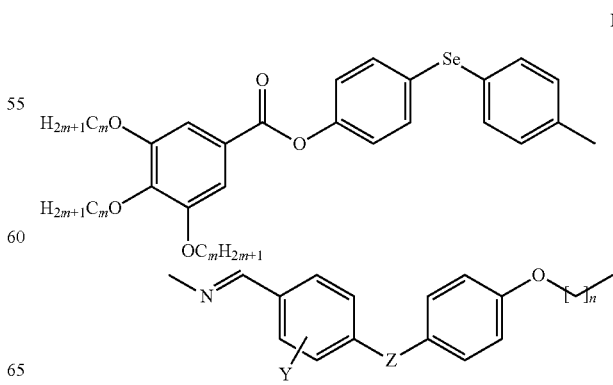

wherein:
Z is O, N, S, or Se;
Y is H, COOH, COOMe, COOEt, $NO_2$, CN, F, Cl, Me, Et, OMe, or OEt;
m is an integer between 6 and 10; and
n is an integer from 2 to 18.

2. The Schiff base organoselenium-based liquid crystal of claim 1, wherein:
Z is O;
Y is H;
m is 10; and
n is 4.

3. The Schiff base organoselenium-based liquid crystal of claim 1, having the formula:

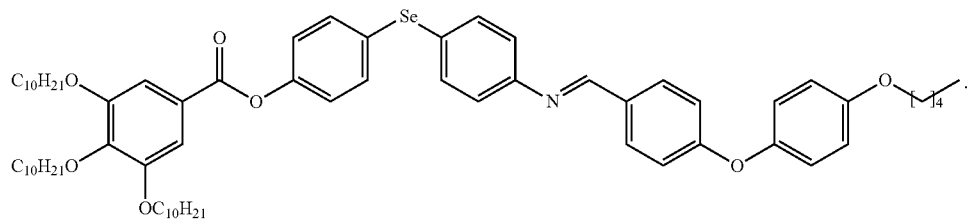

4. A method of making the Schiff base organoselenium-based liquid crystal of claim 1, the method comprising:
1) Reacting a 4-halobenzaldehyde with an alkyloxy phenyl in DMSO to obtain an aldehyde according to the following reaction scheme:

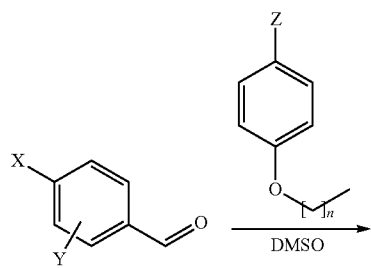

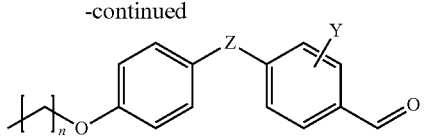

-continued wherein:
X is F or I;
Z is O, N, S, or Se;
Y is H, COOH, COOMe, COOEt, $NO_2$, CN, F, Cl, Me, Et, OMe, or OEt;
m is an integer between 6 and 10; and
n is an integer from 2 to 18;

2) Reacting the aldehyde with 4,4'-diselanediyldianiline in ethanol with catalytic amounts of acetic acid to obtain a bis-Schiff base according to the following reaction scheme:

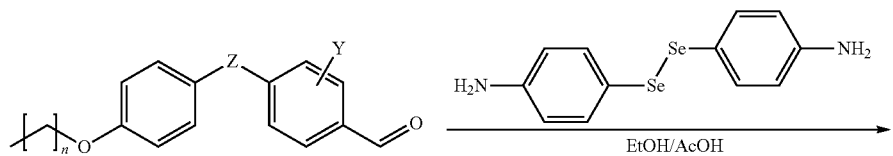

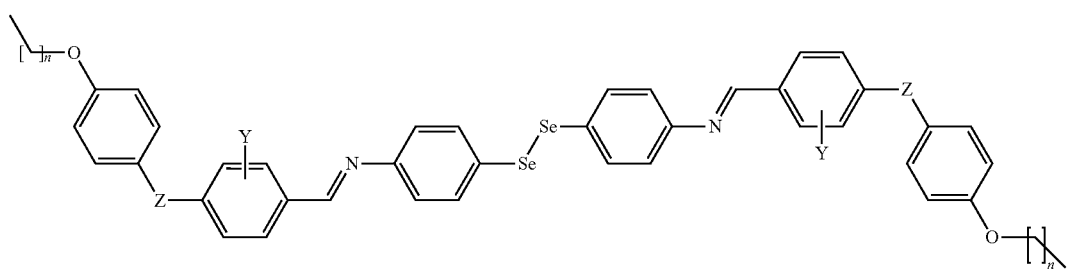

3) Reacting the bis-Schiff base with a halophenyl with copper iron oxide and KOH as catalysts in DMSO to obtain a selenide according to the following reaction scheme:

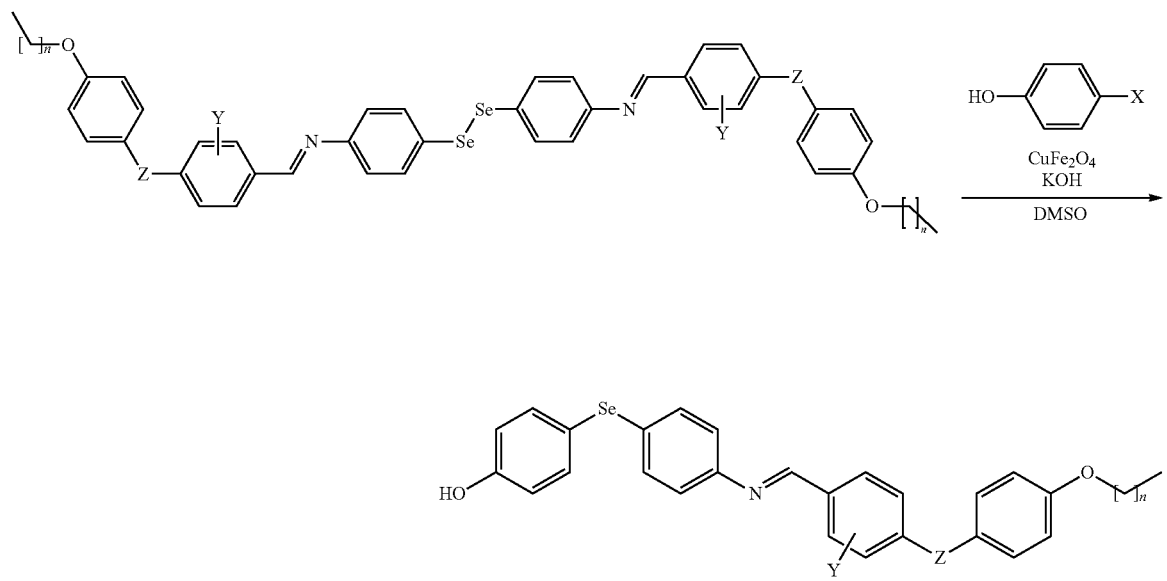

and

4) Heating a tri-substituted benzoic acid with $SOCl_2$ in dichloromethane, followed by reaction with the selenide using triethylamine and a catalytic amount of dry pyridine to obtain the Schiff base organoselenium-based liquid crystal of claim 1 according to the following reaction scheme:

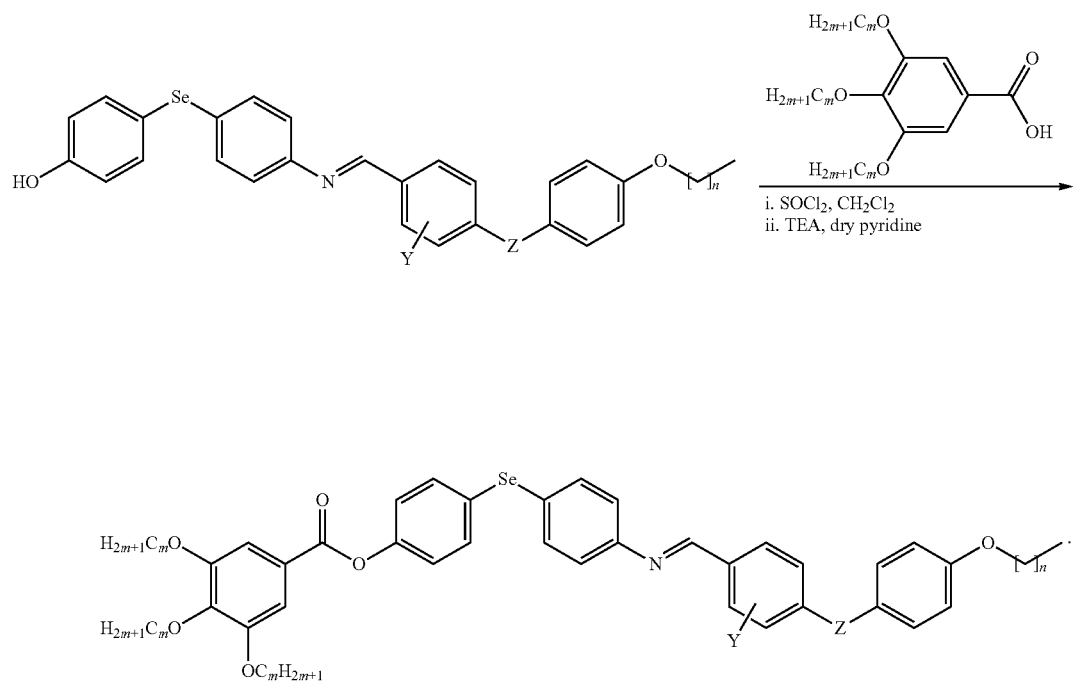

5. The method of claim 4, wherein in step 1, the 4-halobenzaldehyde and the alkyloxy phenyl are reacted in an about 1:1 molar ratio under nitrogen and at a temperature of about 70° C. to about 90° C.

6. The method of claim 4, wherein in step 2, 0.5 equivalents of the 4,4'-diselanediyldianiline are used.

7. The method of claim 4, wherein in step 3, the bis-Schiff base and the halophenyl are reacted in an about 1:2 molar ratio at a temperature of about 110° C. to about 130° C.

8. The method of claim 4, wherein in step 4, the tri-substituted benzoic acid and the $SOCl_2$ in the dichloromethane are heated at a temperature of about 35° C. to about 45° C., with the tri-substituted benzoic acid, the $SOCl_2$, and the selenide being reacted in an about 1:3:0.9 molar ratio.

9. A diazo organoselenium-based liquid crystal having the formula II:

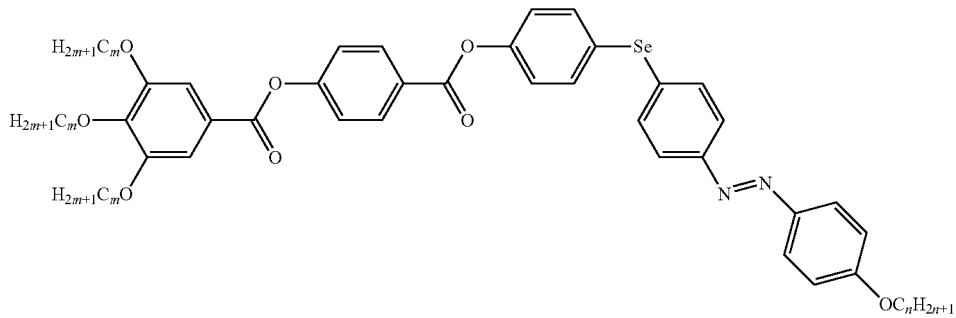

II wherein:
m is an integer between 6 and 10; and
n is an integer from 4 to 20.

10. The diazo organoselenium-based liquid crystal of claim 9, wherein:
m is 10; and
n is 5.

11. The diazo organoselenium-based liquid crystal according to claim 9, having the formula:

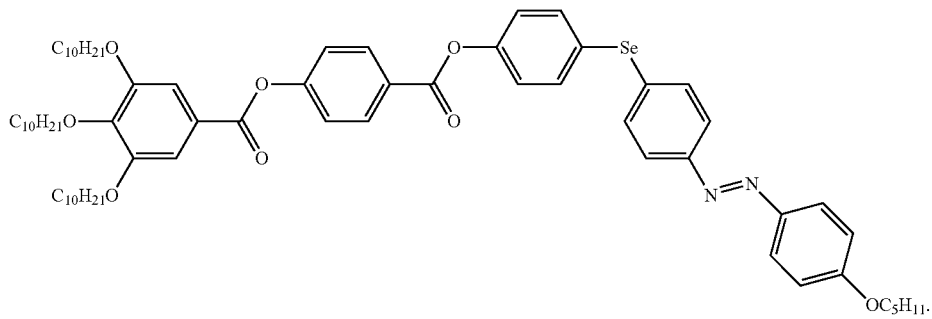

12. A method of making the diazo organoselenium-based liquid crystal of claim 9, the method comprising:
1) Bis diazo-coupling a diselenide diamine and a phenol using NaNO$_2$ and HCl to obtain a first diselenide according to the following reaction scheme:

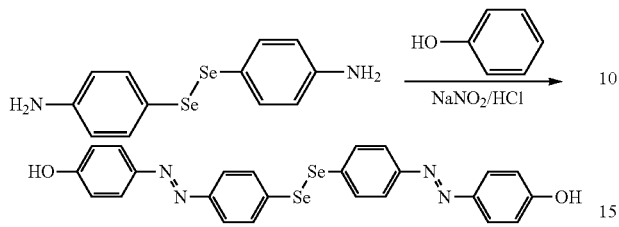

2) Reacting the first diselenide with an alkyl bromide in 2-butanone using K$_2$CO$_3$ as a catalyst with heating at a temperature of about 80° C., followed by reaction in ethanol with KOH with heating at a temperature of about 85° C. to obtain a second diselenide according to the following reaction scheme:

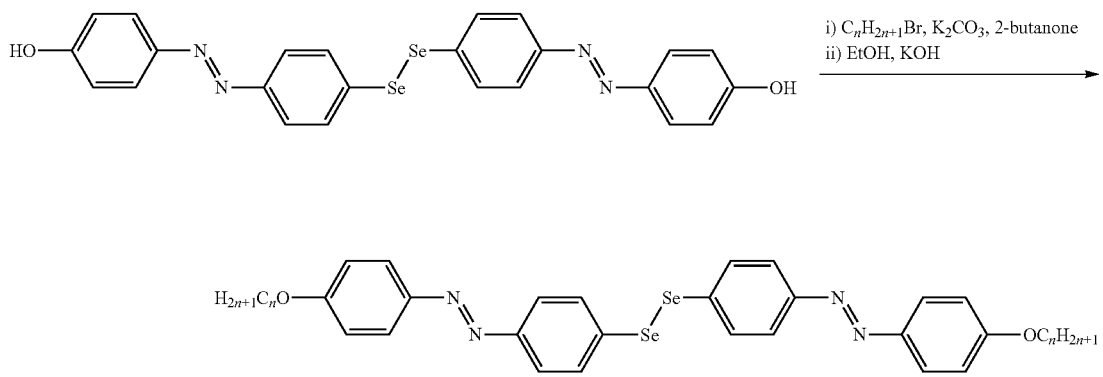

wherein:
m is an integer between 6 and 10; and
n is an integer from 4 to 20;
3) Reacting the second diselenide with 4-iodophenyl and copper iron oxide and KOH as catalysts in DMSO to obtain a selenide according to the following reaction scheme:

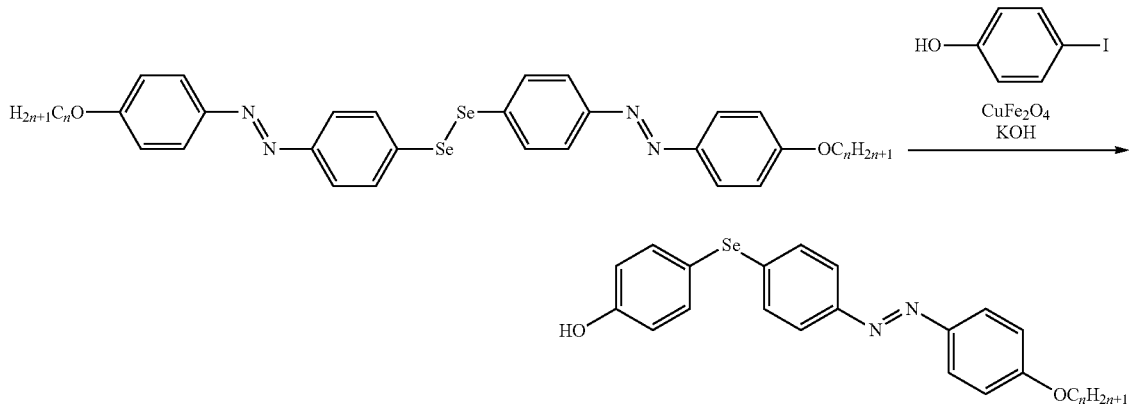

4) Reacting a first trisubstituted benzoic acid with 4-formyl benzoic acid using dicyclohexyl carbodiimide (DCC) followed by oxidation using $CrO_3$ as a catalyst to obtain a second trisubstituted benzoic acid according to the following reaction scheme:

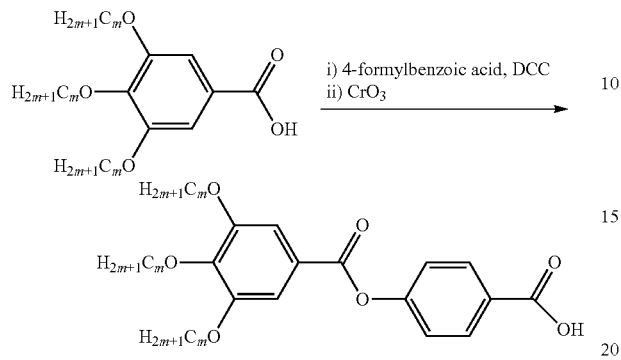

and

5) Heating the second trisubstituted benzoic acid with $SOCl_2$ in dichloromethane followed by reacting with the selenide using triethylamine and a catalytic amount of dry pyridine to obtain the diazo organoselenium-based liquid crystal of claim 9 according to the following reaction scheme:

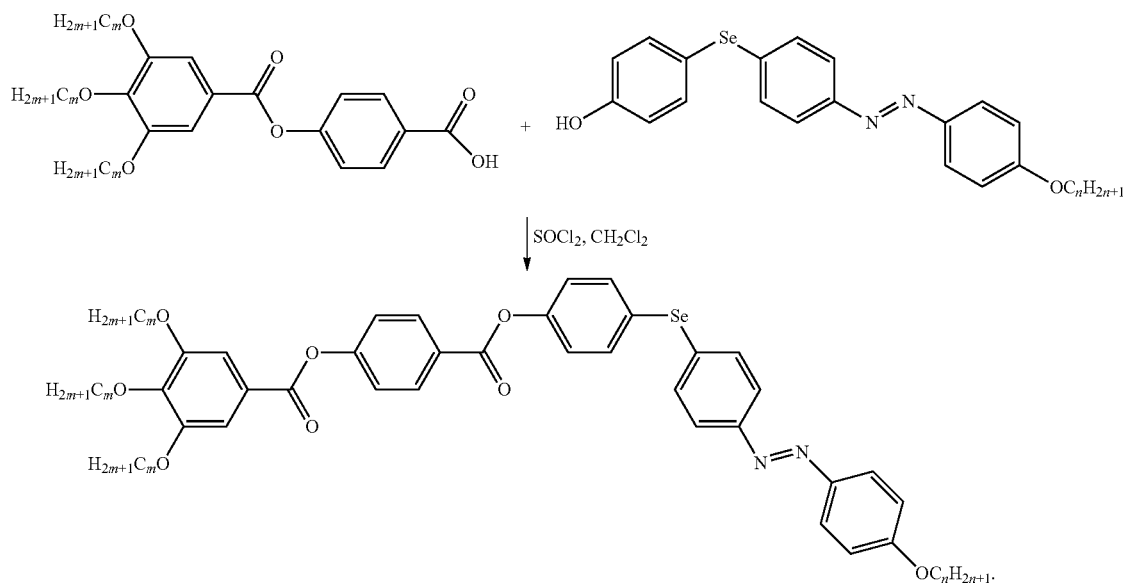

13. The method of claim 12, wherein in step 1, the diselenide diamine and the phenol are reacted in an about 1:2.2 molar ratio.

14. The method of claim 12, wherein in step 2, the first diselenide and the alkyl bromide are reacted in an about 1:2.2 molar ratio.

15. The method of claim 12, wherein step 3 is conducted at a temperature of about 110° C. to about 130° C.

16. The method of claim 12, wherein in step 5, the second trisubstituted benzoic acid and the $SOCl_2$ in the dichloromethane are heated at a temperature of about 35° C. to about 45° C., with the trisubstituted benzoic acid, the $SOCl_2$, and the selenide being reacted in an about 1:3:0.9 molar ratio.

17. A semiconducting liquid crystalline material comprising the Schiff base organoselenium-based liquid crystal of claim 1.

18. The semiconducting liquid crystalline material of claim 17, being a stimuli-responsive material for photophysical applications.

19. A semiconducting liquid crystalline material comprising the diazo organoselenium-based liquid crystal of claim 9.

20. The semiconducting liquid crystalline material of claim 19, being a stimuli-responsive material for photophysical applications.

* * * * *